(12) United States Patent
Fang et al.

(10) Patent No.: US 7,750,138 B2
(45) Date of Patent: Jul. 6, 2010

(54) ANGIOGENESIS-INHIBITING CHIMERIC PROTEIN AND THE USE

(75) Inventors: Jianmin Fang, Shanghai (CN); Zheng Liu, Nanjing (CN); Dechao Yu, Chengdu (CN)

(73) Assignee: Chengdu Kanghong Biotechnologies Co. Ltd., Chengdu, Sichuan (CN)

( * ) Notice: Subject to any disclaimer, the term of this patent is extended or adjusted under 35 U.S.C. 154(b) by 483 days.

(21) Appl. No.: 11/628,735

(22) PCT Filed: Jun. 8, 2005

(86) PCT No.: PCT/CN2005/000802

§ 371 (c)(1),
(2), (4) Date: Dec. 7, 2006

(87) PCT Pub. No.: WO2005/121176

PCT Pub. Date: Dec. 22, 2005

(65) Prior Publication Data

US 2008/0206238 A1    Aug. 28, 2008

(30) Foreign Application Priority Data

Jun. 8, 2004    (CN) .................... 2004 1 0044965

(51) Int. Cl.
*C07H 21/04*    (2006.01)
*C12N 15/00*    (2006.01)
*C12N 5/00*    (2006.01)
*C12P 21/08*    (2006.01)
*A61K 39/395*    (2006.01)

(52) U.S. Cl. .................... 536/23.5; 435/320.1; 435/325; 530/387.3

(58) Field of Classification Search ................ 536/23.5; 435/320.1, 325; 530/387.3
See application file for complete search history.

(56) References Cited

U.S. PATENT DOCUMENTS

| 6,057,428 A | 5/2000 | Keyt et al. |
| 6,100,071 A * | 8/2000 | Davis-Smyth et al. ..... 435/69.7 |
| 2005/0196396 A1 * | 9/2005 | Chen et al. ................ 424/145.1 |

FOREIGN PATENT DOCUMENTS

CN    101134777    *    3/2008

* cited by examiner

*Primary Examiner*—Lynn Bristol
(74) *Attorney, Agent, or Firm*—The Nath Law Group; Susanne M. Hopkins; Charles D. Niebylski

(57) ABSTRACT

The present invention is directed to DNA sequence encoding angiogenesis-inhibiting recombinant chimeric protein, the chimeric protein per se, the pharmaceutical use of the chimeric protein, and to the pharmaceutical composition containing the recombinant protein and the formulation thereof.

6 Claims, 3 Drawing Sheets

ANGIOGENESIS-INHIBITING CHIMERIC PROTEIN AND THE USE

FIELD OF INVENTION

The present invention relates to gene engineering technology, more specifically to DNA sequences encoding angiogenesis-inhibiting recombinant chimeric proteins, the encoded chimeric proteins herein, therapeutic applications thereof, medical composition and formulation containing the chimeric proteins.

BACKGROUND OF INVENTION

Angiogenesis is a process of growing new blood vessels from existing blood vessels. Most adult vascular system is quiescence, angiogenesis only occurs in some physiological and pathological mechanisms, such as tumor, diabetic retinopathies, arthritis, anemia organs, endometrial hyperplasia, etc. Angiogenesis plays key roles in rapid growth of tumor cells during tumor development (Hanahan and Folkman: Patterns and emerging mechanisms of the angiogenic switch during tumorigenesis, Cell, 1996, 86:353-364). Studies of animal cancer models and human clinical trials have already proved that inhibition of tumor angiogenesis could effectively inhibit tumor growth and development, therefore prolong patient's life. Angiogenesis is mediated and regulated by many biological factors. Main cells mediating angiogenesis are vascular endothelial cells that form the inside wall of blood vessels. Various growth factors can bind to relevant receptors on the surface of vascular endothelial cells, regulate cellular processes via intracellular signal transduction, and therefore mediate angiogenesis.

Among various growth factors, VEGF (vascular endothelial cell growth factor) is the most important angiogenesis factor (Ferrara: VEGF and the quest for tumor angiogenesis factor, Nat. Rev. Cancer, 2002, 10: 795-803; Ferrara: Role of vascular endothelial growth factor in physiologic and pathologic angiogenesis: therapeutic implications, Semin. Oncol., 2002, 29 (6 suppl): 10-14). VEGF could be secreted by many types of cells, but often over-expressed in tumor cells. VEGF functions by binding to appropriate receptors. There are mainly two kinds of VEGF receptors: FLT-1 (fms-like tyrosine kinase) and KDR. In terms of molecular structures, these two receptors both consist of three different functional regions: the first region is the extracellular region, consisting of seven immunoglobulin-like (Ig-like) domains (d1-d7), which has specific affinity to VEGF, and is the key region for binding VEGF; the second region is the trans-membrane region containing hydrophobic amino acid residues; the third region is the intracellular domain that contains tyrosine kinase functioning group, which gets phosphorylated after the receptor is activated by VEGF, triggering the intracellular signal transduction, leading to functional effects of endothelial cells and angiogenesis.

FLT-1 and KDR are mainly distributed in vascular endothelial cells. Thus, VEGF's mediating activity to vascular endothelial cells is highly specific. VEGF promotes endothelial cell differentiations, guides endothelial cell migrations, inhibits apoptosis, induces vascular morphological changes, and is a highly effective pro-angiogenesis factor.

The expression level of VEGF in tumor tissues is higher than that in the normal tissues. In addition, rapid growth of tumor cells often leads to hypoxia inside the tumor, and hypoxia further induces expression of VEGF. Thus, VEGF is the key factor promoting tumor angiogenesis. Many animal studies have shown that inhibiting binding of VEGF to its receptors could effectively inhibit tumor angiogenesis, and therefore inhibit tumor growth. In other angiogenesis-related diseases, such as diabetic retinopathies and arthritis, etc, VEGF is also closely involved in the development of these diseases (Ferrara: Role of vascular endothelial growth factor in physiologic and pathologic angiogenesis: therapeutic implications. Semin. Oncol. 2002, 29 (6 suppl): 10-14).

Because of the critical roles of VEGF in cancers and other diseases, proteins or chemicals that specifically inhibit VEGF have therapeutic potentials. For example, studies have shown that neutralizing antibody against VEGF could effectively inhibit tumor growth (Jain: Tumor angiogenesis and accessibility: role of vascular endothelial growth factor, Semin. Oncol., 2002, 29 (6 suppl): 3-9). Therefore, developing novel effective VEGF inhibitors is important in clinical research. Since FLT-1 and KDR are natural binders of VEGF, there were studies that investigated the anti-angiogenesis roles of the soluble FLT-1 (the extracellular domain of FLT-1) and the soluble KDR (the extracellular domain of KDR) (Yoko Hasumi: Soluble FLT-1 Expression Suppresses Carcinomatous Ascites in Nude Mice Bearing Ovarian Cancer. Cancer Research 62, 2002: 2019-2023). The soluble FLT-1 could effectively inhibit growth of vascular endothelial cells in vitro, but it has a short serum half-life and can not reach effective serum concentration. Similarly, the soluble KDR was also able to inhibit growth of vascular endothelial cells in vitro, but its anti-tumor activity in animal models was not satisfactory (Yoko Hasumi: Soluble FLT-1 Expression Suppresses Carcinomatous Ascites in Nude Mice Bearing Ovarian Cancer. Cancer Research 62, 2002: 2019-2023).

To overcome the shortcomings of the prior art, the present invention provides novel chimeric proteins containing different fragments of FLT-1 and KDR to effectively block the biological activity of VEGF and inhibit angiogenesis.

SUMMARY OF INVENTION

The first aspect of the invention is to provide novel recombinant chimeric proteins that block the biological activity of VEGF and inhibit angiogenesis.

The second aspect of the invention is to provide DNA sequences encoding the above-mentioned chimeric proteins.

The third aspect of the invention is to provide vectors containing the coding DNA sequences of the chimeric proteins and recombinant hosts thereof.

The fourth aspect of the invention is to provide the use of the chimeric proteins in preparing medicaments that block the VEGF activity and inhibit angiogenesis, and medical composition containing the chimeric proteins and appropriate medical carriers and dosage form thereof, as well as therapeutic applications of the medical composition.

Key points of the invention are to design and construct a series of chimeric proteins with different FLT-1 or KDR fragments, which preferably contain human immunoglobulin Fc (construction method is shown in FIG. 1), and then to select the chimeric protein with high affinity to VEGF using assays including the VEGF binding assay, and finally to obtain the proper VEGF inhibitor. Construction of the chimeric protein is based on the conventional molecular cloning technologies. Detailed experimental methodology could be found in laboratory manuals such as *Molecular Cloning*, the $2^{nd}$ or the $3^{rd}$ edition (Joseph Sambrook).

According to the present invention, the chimeric proteins made via recombinant DNA technology contain different fragments of the VEGF receptors FLT-1 and KDR, wherein the chimeric proteins are selected from the following groups:

a. Consisting of the $1^{st}$ Ig-like domain of KDR, the $2^{nd}$ Ig-like domain of FLT-1, and the $3^{rd}$ Ig-like domain of KDR, designated as KDRd1-FLTd2-KDRd3;
b. Consisting of the $2^{nd}$ Ig-like domain of FLT-1, and the $3^{rd}$ and the $4^{th}$ Ig-like domains of KDR, designated as FLTd2-KDRd3,4;
c. Consisting of the $2^{nd}$ Ig-like domain of FLT-1, the $3^{rd}$ Ig-like domain of KDR, and the $4^{th}$ Ig-like domain of FLT-1, designated as FLTd2-KDRd3-FLTd4;
d. Consisting of the $2^{nd}$ Ig-like domain of FLT-1, and the $3^{rd}$, the $4^{th}$ and the $5^{th}$ Ig-like domains of KDR, designated as FLTd2-KDRd3,4,5;
e. Consisting of the $2^{nd}$ Ig-like domain of FLT-1, the $3^{rd}$ Ig-like domain of KDR, and the $4^{th}$ and the $5^{th}$ Ig-like domains of FLT-1, designated as FLTd2-KDRd3-FLTd4,5.

The amino acid sequence of FLTd2 is shown as SEQ ID NO.1. The amino acid sequence of FLTd4 is shown as SEQ ID NO.2. The amino acid sequence of KDRd1 is shown as SEQ ID NO.3. The amino acid sequence of KDRd3 is shown as SEQ ID NO.4. The amino acid sequence of KDRd4 is shown as SEQ ID NO.5.

As used herein, FLT refers to the FLT-1 sequence, KDR refers to the KDR sequence; di refers to the $i^{th}$ Ig-like domain in FLT-1 or KDR.

Preferably, the present invention provides a class of chimeric proteins that contain human immunoglobulin Fc, and are preferably selected from the following groups:
FP2' designated as KDRd1-FLTd2-KDRd3-Fc;
FP3' designated as FLTd2-KDRd3,4-Fc;
FP4' designated as FLTd2-KDRd3-FLTd4-Fc;
FP5' designated as FLTd2-KDRd3,4,5-Fc;
FP6' designated as FLTd2-KDRd3-FLTd4,5-Fc.

As used herein, Fc refers to the human immunoglobulin Fc fragment derived from human immunoglobulin FC such as IgG, IgM, and IgA, or subclasses IgG1, IgG2, IgG3, and IgG4. The Fc region can be the full length Fc sequence or a fragment of the Fc sequence from CH2, CH3, or the hinge region.

As shown in FIG. 1, the chimeric protein known in the prior art (designated as FP1') consists of the $2^{nd}$ Ig-like domain of FLT-1 (FLTd2), the $3^{rd}$ Ig-like domain of KDR (KDRd3), and the human immunoglobulin Fc. The chimeric protein FP2' provided in the invention has added amino acid sequence of the $1^{st}$ Ig-like domain of KDR (KDRd1) into FP1', which increases binding sites for VEGF and enhances affinity to VEGF. The chimeric proteins FP3' and FP4' have added sequences of the $4^{th}$ Ig-like domain of KDR (KDRd4) or the $4^{th}$ Ig-like domain of FLT-1 (FLTd4) based on FP1', respectively. FP5' and FP6' have added the $4^{th}$ and the $5^{th}$ Ig-like domains of KDR (KDRd4, 5) and the $4^{th}$ and the $5^{th}$ Ig-like domains of FLT-1 (FLT-1d4, 5) based on FP1', respectively. These added sequences could help dimerization of the chimeric proteins, folding 3-dimensional structures favorable for VEGF binding, and enhancing affinity to VEGF.

More preferably, the present invention provides a chimeric protein FP3' with amino acid sequence shown as SEQ ID NO.7.

The chimeric proteins described in the invention can be obtained through conventional recombinant DNA technologies. At first, recombinant DNA coding sequences of the above mentioned chimeric proteins could be obtained, wherein the coding DNA sequences of FLT-1 and KDR are available in GenBank, NCBI (National Center for Biotechnology Information). Secondly, the DNA coding sequences of the above-mentioned chimeric proteins are cloned into vectors after PCR synthesis. The vectors herein could be commonly used plasmids, viruses, or DNA fragments in molecular biology. Secretory signal sequence is inserted into the terminal of the DNA sequence of the aforesaid chimeric peptides to ensure secretion out of cells. The vector sequence includes a promoter region that enables gene transcription, starting and stopping signals for protein translation, and a polyA sequence. The vector contains an antibiotics resistant gene for propagation in bacteria. In addition, the vector contains a eukaryotic cell selection gene for selection of stable transfected cell lines.

Because there is no absolute boundary of the amino acid sequences of all Ig-like domains in FLT-1 and KDR, the sequence length of these domains could have variations. Thus the sequences of the chimeric proteins described in the invention could have similar variations. It should be appreciated that all of these sequence variants are not to be considered as beyond the scope of the invention.

After plasmids construction of the above-mentioned chimeric proteins, the plasmids could be used to transfect host cells to express the chimeric proteins. There are many expression systems for these chimeric proteins, including (but not limited to) mammalian cells, bacteria, yeast, and insect cells. Among them, mammalian and insect cells are eukaryotic cells, whereas bacteria and yeast cells are prokaryotic cells. Proteins expressed from mammalian cells are glycosylated. Since the chimeric proteins of the invention contain glycosylation sites, mammalian cells are the best cells to express them. There are many mammalian cell types suitable for large scale protein productions, such as 293 cells, CHO cells, SP20 cells, NS0 cells, COS cells, BHK cells, PerC6 cells, and etc. Many other types of cells could also be used to express and produce these proteins, and they are all within the scope of the invention. Plasmids encoding the above-mentioned chimeric proteins could be transfected into the cells. Methods of transfection include, but not limited to, electroporation, liposome-mediated transfection, Calcium precipitation, and etc.

Expression systems other than mammalian cells could also be used to express these chimeric proteins, such as bacteria, yeast, insect cells, and etc. They should all be considered as within the scope of the invention. These expression systems have a higher protein production yield comparing with that of mammalian cells, however, they produce proteins with no glycosylation or with carbohydrate chains glycosylated different from that of mammalian cells.

After expression of the chimeric proteins, the chimeric proteins concentrations in the cell culture media could be measured by ELISA or other assays. Since the chimeric proteins contain the immunoglobulin Fc region, they could be purified using Protein A affinity chromatography.

After various chimeric proteins were obtained from culture media of the recombinant host cells, they were assayed in VEGF binding experiments to compare their affinities to VEGF. Their VEGF inhibition activities were further assayed in a VEGF-induced human vascular endothelial cell proliferation experiment. The experimental results have shown that all chimeric proteins constructed according to the present invention can bind to VEGF with high affinities (FIG. 2), comparing with the FP1' of the prior art. In addition, they could effectively block the VEGF activation of the vascular endothelial cells and inhibit growth of the endothelial cells. Further experiments have shown that FP3' has the best blocking activity on VEGF and is the most effective VEGF-blocking chimeric proteins of the invention.

Thus, the chimeric proteins constructed in the invention have supreme blocking activities on VEGF, and all have biological activities of anti-angiogenesis, therefore can be used to treat angiogenesis or VEGF related diseases, including but not limited to various tumor, diabetic retinopathies, arthritis, anemia, endometrial hyperplasia, etc.

In order to further substantiate the anti-angiogenesis effect of the chimeric proteins in vivo, some animal model experiments have also been made. The results of these experiments have shown that in B16F10 melanoma BALB/C nude mouse model and human PC-3 prostate tumor xenograft mouse model, the chimeric proteins of the invention have been much better than FP1' of the prior art, and effectively inhibited tumor growth and prolonged animal life. Thus, the chimeric proteins of the invention are of high anti-cancer activities.

The present invention also provides medical compositions comprising the above-described chimeric proteins and appropriate medical carriers. Said compositions can be formulated into any dosage forms according to conventional formulation methodologies, preferably into a dosage form for injection, and more preferably into a lyophilized format.

SPECIFIC EMBODIMENTS

The following examples provide detailed description of construction, experimental methodology and application of the chimeric proteins described in the invention. But these examples should not be construed to limit the protection scope of the invention.

Figure 1:
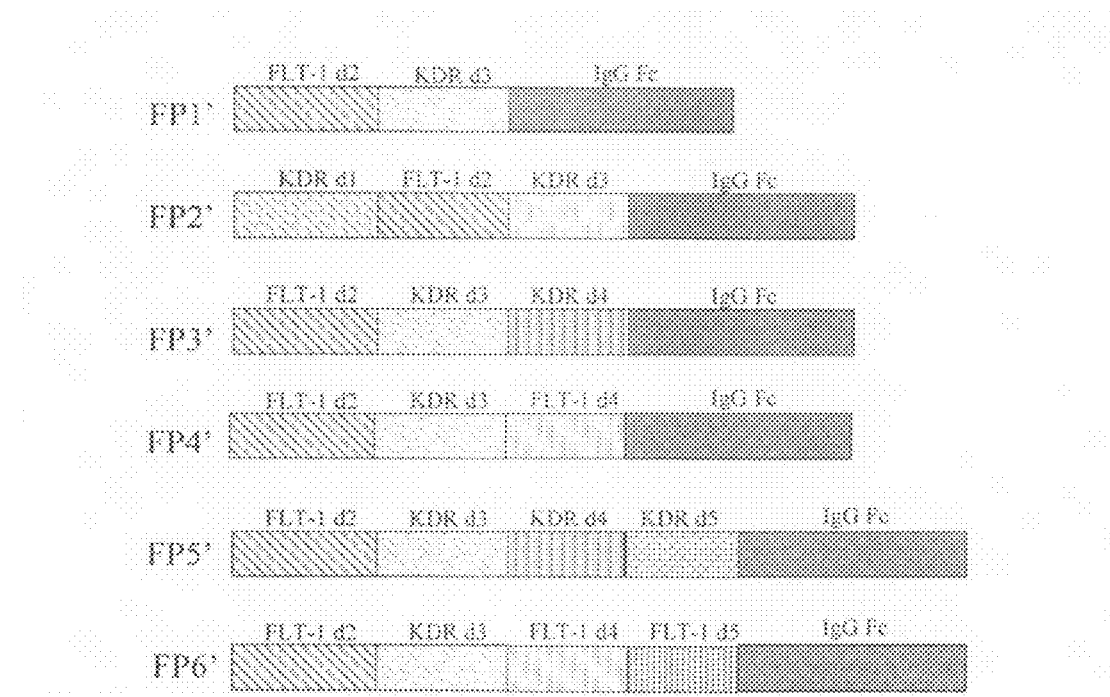
FIG. 1 shows the structures of the five chimeric proteins according to a preferred embodiment of the invention and FP1' of the prior art. They are constructed with different fragments from FLT-1, KDR and the immunoglobulin Fc region using genic engineering technologies.

Embodiment 1: Cloning of the DNA Sequences Encoding the Chimeric Proteins and Construction of the Recombinant Vectors Other than the immunoglobulin Fc coding DNA sequence, coding DNA sequences of the various chimeric proteins of the invention come from cDNAs of FLT-1 and KDR. Since FLT-1 and KDR are mainly expressed in vascular endothelial cells, the total RNA were extracted from human umbilical vein endothelial cells (HUVEC) using a RNA purification kit (QIAGEN); then cDNAs were synthesized from the RNA using AMV Reverse Transcriptese (Promega); then various FLT-1 and KDR fragments were PCR amplified with different primers; finally the sequences from FLT-1, KDR, and human immunoglobulin Fc (IgG1 Fc) were fused together by PCR to construct recombinant DNA sequences encoding various chimeric proteins. Structures of all six chimeric proteins (including FP1' of the prior art) are shown in FIG. 1.

EXAMPLE 1

Construction of FP3' Coding Sequence and Recombinant Vector

HUVEC cells (Clonetics) were cultured with EGM-2 media (Clonetics) in T-175 flasks. $1 \times 10^7$ cells were collected and subjected to the total RNA extraction using the RNA purification kit from Qiagen, and then cDNA was synthesized using the Invitrogen cDNA kit. The cDNA product was stored at $-80°$ C. until usage. Following specific primers were used to PCR amplify various FLT-1 and KDR domains from the HUVEC cDNA.

PCR utilizing specific primers were used to amplify various FLT-1 and KDR domains from the HUVEC cDNA. Likewise, PCR utilizing specific primers from Lymph Nodes cDNA (BD Clontech) were used to amplify human IgG1 Fc was PCR.

The specific primers used are as follows:

for FLT-1 d2 forward: 5'-cctttcgtagagatgtacagtga-3' (SEQ ID NO: 8);

for FLT-1 d2 reverse: 5'-tatgattgtattggtttgtccat-3' (SEQ ID NO: 9);

for KDR d3-4 forward: 5'-gatgtggttctgagtccgtctca-3' (SEQ ID NO: 10);

for KDR d3-4 reverse: 5'-cggtgggacatacacaaccaga-3' (SEQ ID NO: 11);

for human IgG1 Fc forward: 5'-gacaaaactcacacatgcccact-3' (SEQ ID NO: 12); and for human IgG1 Fc reverse: 5'-tcatttacccggagacagggagag-3' (SEQ ID NO: 13).

The Ig-like domains and the human IgG1 Fc fragment were PCR amplified at conditions of denaturing at $95°$ C. for 30 seconds, annealing at $56°$ C. for 45 seconds, extension at $72°$ C. for 2 minutes, and 30 cycles. The PCR products were then cloned into plasmid pCR2.1 (Invitrogen) using the TA cloning kit. After transformation into E. coli (JM109), white colonies were picked and cultured overnight in LB media. DNA plasmids were prepared using the Qiagen kit and subjected to enzyme digestion and DNA sequencing.

The cDNAs of FLT-1, KDR and IgG Fc were fused together by sewing PCR using primers containing the EcoRI site. After digestion with EcoRI, the DNA fragment was purified with the Qiagen purification kit and cloned into plasmid pcDNA3.1. After transformed into E. coli (JM 109), positive colonies were picked and cultured overnight in LB media. DNA plasmids were extracted with the Qiagen plasmid purification kit and then subjected to enzyme digestion and DNA sequencing. The obtained FP3' DNA coding sequence is shown as SEQ ID NO.6. The confirmed plasmids were used to transfect 293 cells or CHO cells to obtain stable cell lines expressing FP3'. The amino acid sequence of FP3' is shown as SEQ ID NO.7.

EXAMPLE 2

Construction of FP1' Gene and Recombinant Vector

FP1' was constructed similarly as in Example 1. The only difference was that the targeted recombinant DNA was constructed by fusing together the 2$^{nd}$ Ig-like domain of FLT-1, the 3$^{rd}$ Ig-like domain of KDR, and the same human IgG1 Fc as in Example 1.

EXAMPLE 3

Construction of FP2' Gene and Recombinant Vector

FP2' was constructed similarly as in Example 1. The only difference was that the targeted recombinant DNA was constructed by fusing together the 1$^{st}$ Ig-like domain of KDR, the 2$^{nd}$ Ig-like domain of FLT-1, the 3$^{rd}$ Ig-like domain of KDR, and the same human IgG1 Fc as in Example 1.

EXAMPLE 4

Construction of FP4' Gene and Recombinant Vector

FP4' was constructed similarly as in Example 1. The only difference was that the targeted recombinant DNA was constructed by fusing together the 2$^{nd}$ Ig-like domain of FLT-1, the 3$^{rd}$ Ig-like domain of KDR, the 4$^{th}$ Ig-like domain of FLT-1, and the same human IgG1 Fc as in Example 1.

EXAMPLE 5

Construction of FP5' Gene and Recombinant Vector

FP5' was constructed similarly as in Example 1. The only difference was that the targeted recombinant DNA was constructed by fusing together the 2$^{nd}$ Ig-like domain of FLT-1, the 3$^{rd}$-5$^{th}$ Ig-like domain of KDR, and the same human IgG1 Fc as in Example 1.

EXAMPLE 6

Construction of FP6' Gene and Recombinant Vector

FP6' was constructed similarly as in Example 1. The only difference was that the targeted recombinant DNA was constructed by fusing together the 2$^{nd}$ Ig-like domain of FLT-1, the 3$^{rd}$ Ig-like domain of KDR, the 4$^{th}$-5$^{th}$ Ig-like domain of FLT-1, and the same human IgG1 Fc as in Example 1.

Embodiment 2: Expression of the Chimeric Proteins in Cells

EXAMPLE 7

Expression of the Chimeric Proteins FP3'

After construction of above-mentioned recombinant plasmids, high quality plasmid DNAs were obtained using Qiagen's plasmid kit, and then were transfected into 293 cells (ATCC) using FUGEN6 transfection kit (Roche). Two different methods were used to express the chimeric proteins depending on amount of proteins needed.

The first method was a method of transient transfection. A small amount of the chimeric proteins were produced using this method. Firstly, 293 cells were cultured in DMEM media with 10% FBS in tissue culture dishes. At 60-80% cell confluence, the mixture of plasmid DNA and FUGEN6 reagent was added into the culture. The culture media was exchanged to serum-free DMEM in the next day and the cells were continued to culture for 3 more days before media was collected. These media contained the expressed chimeric proteins, and the concentration of the chimeric proteins was assayed by ELISA.

The second method was a method of stable transfection. A stable cell line was established to produce a large amount of the chimeric proteins. The host cells were again 293 cells (ATCC). The step of transfecting recombinant plasmid was the same as that of transient transfection described above. However, at the 2$^{nd}$ day, the cells were cultured in DMEM with neomycin and cloned by limited dilution. After about 21 days, neomycin resistant clones were picked and cultured in a larger scale. Finally, chimeric proteins were expressed in shaker flasks. The concentration of chimeric proteins was assayed by ELISA.

FP3' was purified from the cultured media using assays including affinity chromatography and gel filtration, etc. The molecular weight of FP3' was 140 KD.

EXAMPLE 8

Expression of Other Chimeric Proteins

Chimeric proteins FP1', FP2', FP4', FP5', and FP6' were obtained in accordance with the methods of example 7.

Embodiment 3: Binding Experiment of the Chimeric Proteins to VEGF

Affinities of the chimeric proteins to VEGF were determined by the VEGF binding assay in the present invention. Firstly, recombinant VEGF proteins (Chemicom) were coated in a 96-well ELISA plate, and non-specific protein binding sites of the plate were then blocked using 5% milk solution. Secondly, different concentrations of various chimeric proteins were added into each well, and incubated for 2 hours at 37° C. After washing, rabbit anti-human Ig-HRP (Sigma) was added into each well, and finally colorimetric enzyme substrates were added to the plate. The absorption OD readings were recorded with the use of an ELISA plate reader. A higher OD value indicated a stronger binding affinity of the chimeric proteins to VEGF.

Figure 2:
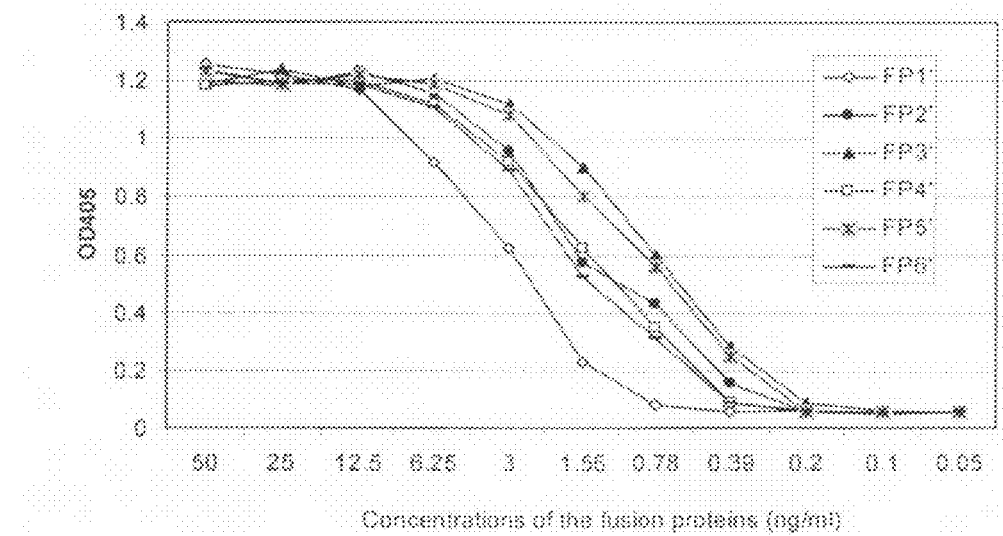
FIG. 2 exhibits the results of VEGF binding of the five chimeric proteins in a preferred embodiment of the invention, in comparison with that of FP1' of the prior art, wherein OD readings refer to the binding signals of chimeric proteins to VEGF. The results have shown that all the five chimeric proteins bound to VEGF with much higher affinities than FP1', among them, FP3' has the highest affinity.

As shown in FIG. 2, all five chimeric proteins constructed and expressed in the embodiments of the present invention were able to bind VEGF, and had better affinities than FP1' of the prior art. The binding was detectable at low concentrations of 1 μg/ml. Preferably, FP3' had the best affinity and was the best VEGF inhibitor. Its half maximal binding concentration was about 5 times lower than that of FP1'. FP5' had a little bit lower affinity to VEGF than that of FP3'. This result suggests that the 4$^{th}$ Ig-like domain of KDR could substantially increase the blocking activity of the chimeric protein to VEGF. However, adding more of the KDR domains such as the 5$^{th}$ Ig-like domain could not further enhance the inhibitory effect on VEGF. The other three chimeric proteins exhibited lower affinities comparing to FP3' and FP5', but higher affinities than FP1'.

Embodiment 4: The Chimeric Proteins Effectively Inhibited Proliferation of Human Vascular Endothelial Cells In Vitro This preferred embodiment of the invention is to prove that the chimeric proteins could effectively block VEGF-induced growth of vascular endothelial cells. In the experiment, HUVEC cells (Clonetics) were seeded in a 96-well tissue culture plate in EBM media with 2% FBS and 15 ng/ml of VEGF. Different amounts of the 293 cells supernatant containing the chimeric proteins were added into the plate. Untransfected 293 cells media containing no chimeric proteins was used as negative control. All HUVEC cells were cultured in 37° C. for 3 days before cell densities were determined by cell counting.

Figure 3:
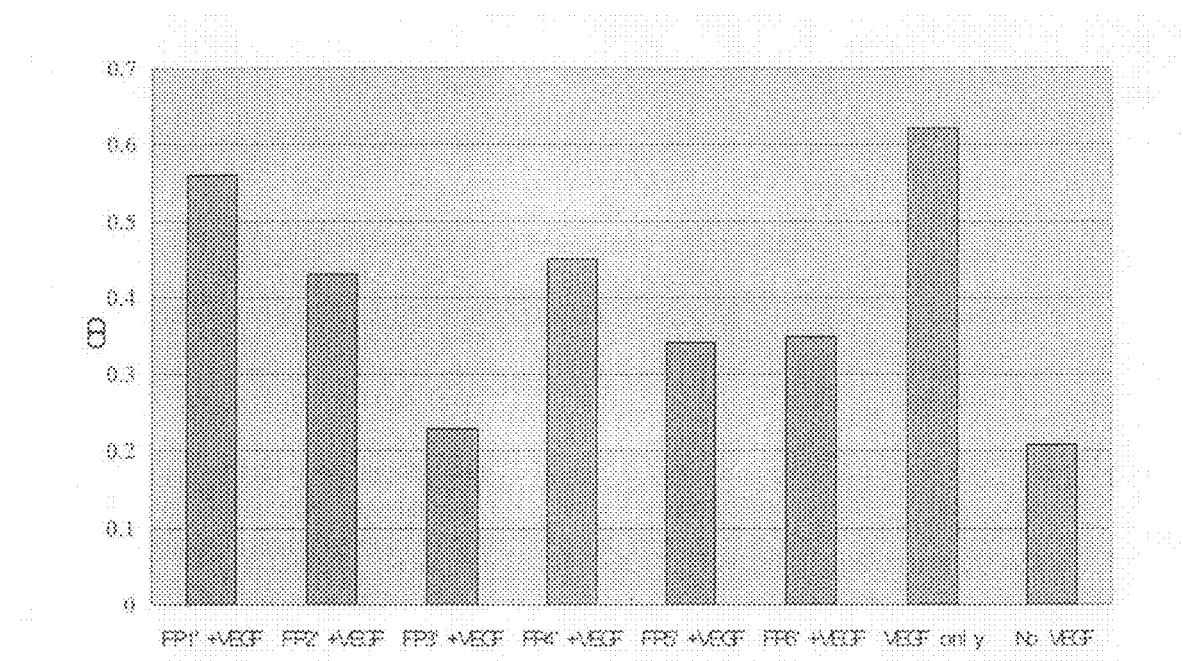
FIG. 3 shows that the chimeric proteins of the invention could effectively inhibit human vascular endothelial cell growth in vitro, in comparison with FP1'.

The HUVEC proliferation experiment has shown that all five chimeric proteins constructed according to the invention could inhibit proliferation of vascular endothelial cells more effectively than FP1' of the prior art (FIG. 3). Since the HUVEC cell proliferation in the experiment was induced by VEGF activation, it is therefore suggested that all five chimeric proteins were able to inhibit the receptor activation of VEGF, and all of them possessed anti-angiogenesis activities. Among which, FP3' had the best inhibiting effect on the HUVEC cell growth with IC50 of about 3 ng/ml. The IC50 of FP1' of the prior art was about 12 ng/ml, and the IC50s of FP2', FP4', FP5', and FP6' were all about 5-8 ng/ml.

Embodiment 5: The Chimeric Polypeptides Inhibited Tumor Growth in Mice

EXAMPLE 9

Preparation of Injection Formulation Containing the Chimeric Proteins

The injection formulation was prepared according to any conventional methodologies, for injection formulations using 24 mg/ml of FP3', 5 mM of PB, 100 mM of NaCl, and 20% sucrose.

EXAMPLE 10

The Chimeric Proteins Effectively Inhibited the Growth of B16F10 Melanoma Cells in Mice As VEGF inhibitors, one application of the chimeric proteins of the invention is to be used in anti-cancer therapy. Because of its highly effective blocking effect on VEGF, FP3' was chosen to perform anti-tumor experiments in animal models.

Figure 4:
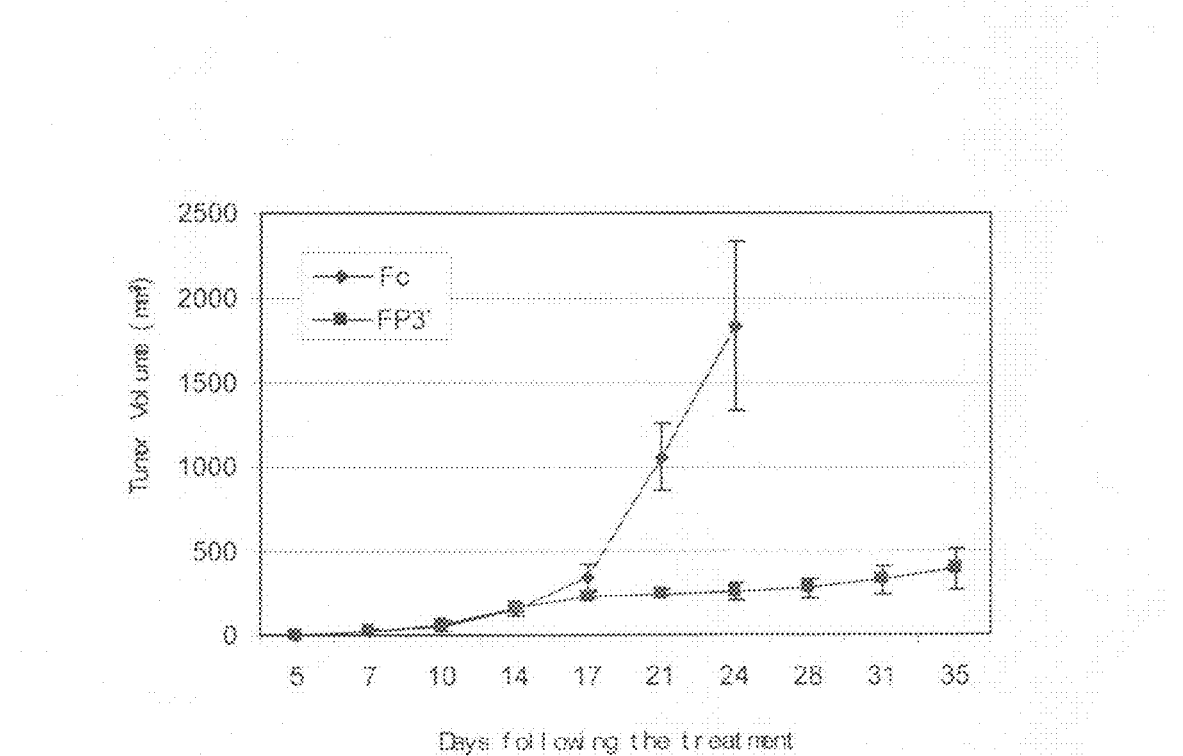
FIG. 4 shows that the chimeric protein FP3' could effectively inhibit B16F10 melanoma tumor growth in mice.

The animal model was murine with B16F10 melanoma cells which is a kind of rapidly growing tumor cells. In the experiment, $1\times10^5$ B16F10 cells in 0.05 ml were first injected subcutaneously in the back of BALB/C nude mice. Then the purified chimeric protein was injected intraperitoneally with 400 μg each mouse (mice average weight 22 g), twice a week. Same amount of the purified human immunoglobulin Fc was injected into negative control mice. Tumor growth curves were shown in FIG. 4, indicating that the chimeric protein FP3' effectively inhibited the growth of the melanoma cells ($P<0.01$).

EXAMPLE 11

Figure 5:
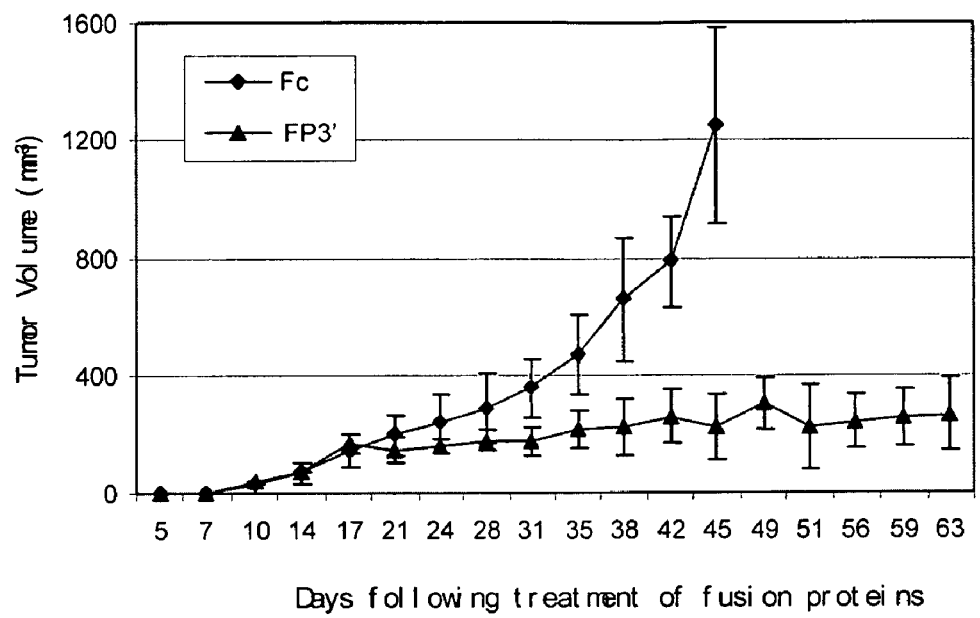
FIG. 5 shows that the chimeric protein FP3 could effectively inhibit human PC-3 prostate tumor growth in mice.

The Chimeric Proteins Effectively Inhibited the Growth of Xenographed Prostate Cancer PC-3 Cells in Mice Xenograft model of human tumor cells growing in nude mice is one of the animal models, which is most similar with human tumors. Nude mice lack of immune rejection, thus many human tumor cells could grow in nude mice and form tumor. The chimeric protein FP3' was tested for inhibiting growth of human prostate tumor PC-3 cells (ATCC) in BALB/C nude mice. In this model, $1\times10^5$ PC-3 cells in 0.05 ml were first injected subcutaneously in the back of mice. Then the purified chimeric protein was injected intraperitoneally with 400 μg each mouse, twice a week. Same amount of the purified human immunoglobulin Fc was injected into negative control mice. The experimental results were shown in FIG. 5. In the control mice, tumor grew more than 1000 $mm^3$ 45 days after implantation. However, in the mice administered with the chimeric proteins, FP3' has almost completely inhibited the tumor growth ($P<0.01$), demonstrating a significant therapeutic anti-tumor effect.

Figure 6:
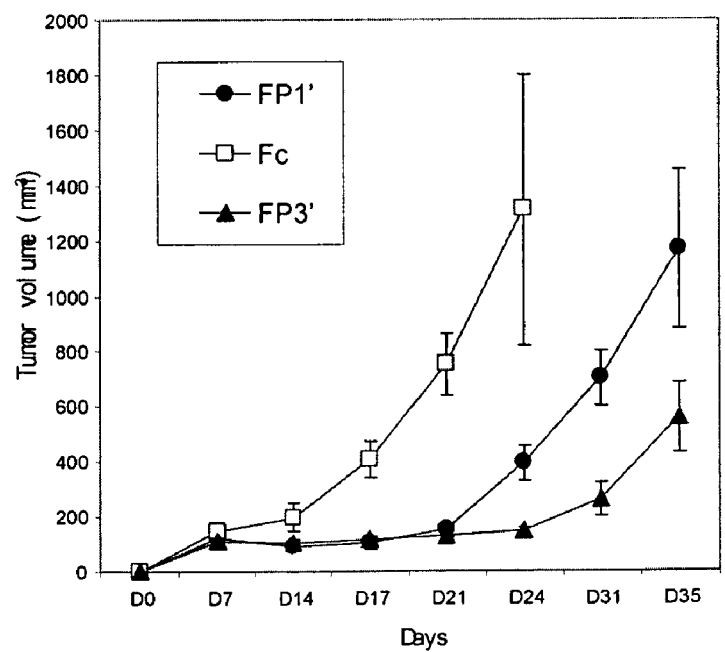
FIG. 6 compares anti-tumor growth activities of the chimeric protein FP3' of the invention with that of FP1' of the prior art in mice.

Embodiment 6: Comparing Study of the Chimeric Protein FP3' and FP1' of the Prior Art in Inhibiting Tumor Growth in Mice In order to further demonstrate the supreme anti-cancer activity of FP3', the effects of FP1' and FP3' were compared in a tumor growth experiment. 10 healthy BALB/C nude mice were chosen and each was injected subcutaneously in the back with $1\times10^5$ rat glioblastoma C6 cells in 0.05 ml. Then 2.5 mg/kg of purified PF1' or PF3' were injected intraperitoneally twice a week, respectively, up to 31 days. The same amount of the purified human immunoglobulin Fc was injected into negative control mice. The experimental results are shown in FIG. 6. FP1' and FP3' both had a significant therapeutic effect on the tumor. At day 35, tumor volumes of mice administered with FP1' and FP3' were 1167.3 and 557.6, respectively, whereas tumor volume of the control mice treated with Fc has already reached 1312.3 at day 24. Therefore, FP3' had more significant effect ($P<0.05$) than FP1' of the prior art.

All taken together, the chimeric proteins constructed according to the invention had a high affinity to VEGF, were able to inhibit vascular endothelial cell proliferation in vitro, and effectively inhibited tumor growth in vivo. Since angiogenesis is critical in all tumor growth, the chimeric proteins of the invention can be used in therapeutic applications against many tumors.

What is claimed is:

1. An isolated recombinant DNA coding sequence encoding the chimeric protein FP3', wherein the DNA sequence is shown as SEQ ID NO. 6.

2. An isolated recombinant vector comprising the recombinant DNA sequence of claim 1, wherein the vector is selected from plasmid, virus, or DNA fragment.

3. An isolated recombinant host cell containing the recombinant vector of claim 2, wherein the host cell is a eukaryotic or prokaryotic cell.

4. A chimeric FP3' protein encoded by a recombinant DNA sequence of SEQ ID NO. 6.

5. A pharmaceutical composition which comprises one or more chimeric proteins according to claim 4, and a pharmaceutically acceptable carrier.

6. The pharmaceutical composition of claim 5, wherein the pharmaceutical composition is an injection solution.

* * * * *

SEQUENCE LISTING

```
<160> NUMBER OF SEQ ID NOS: 13

<210> SEQ ID NO 1
<211> LENGTH: 93
<212> TYPE: PRT
<213> ORGANISM: Homo sapiens

<400> SEQUENCE: 1

Pro Phe Val Glu Met Tyr Ser Glu Ile Pro Glu Ile Ile His Met Thr
1               5                   10                  15
```

Glu Gly Arg Glu Leu Val Ile Pro Cys Arg Val Thr Ser Pro Asn Ile
                20                  25                  30

Thr Val Thr Leu Lys Lys Phe Pro Leu Asp Thr Leu Ile Pro Asp Gly
            35                  40                  45

Lys Arg Ile Ile Trp Asp Ser Arg Lys Gly Phe Ile Ile Ser Asn Ala
    50                  55                  60

Thr Tyr Lys Glu Ile Gly Leu Leu Thr Cys Glu Ala Thr Val Asn Gly
65                  70                  75                  80

His Leu Tyr Lys Thr Asn Tyr Leu Thr His Arg Gln Thr
                85                  90

<210> SEQ ID NO 2
<211> LENGTH: 96
<212> TYPE: PRT
<213> ORGANISM: Homo sapiens

<400> SEQUENCE: 2

Phe Ile Thr Val Lys His Arg Lys Gln Gln Val Leu Glu Thr Val Ala
1               5                   10                  15

Gly Lys Arg Ser Tyr Arg Leu Ser Met Lys Val Lys Ala Phe Pro Ser
                20                  25                  30

Pro Glu Val Val Trp Leu Lys Asp Gly Leu Pro Ala Thr Glu Lys Ser
            35                  40                  45

Ala Arg Tyr Leu Thr Arg Gly Tyr Ser Leu Ile Ile Lys Asp Val Thr
    50                  55                  60

Glu Glu Asp Ala Gly Asn Tyr Thr Ile Leu Leu Ser Ile Lys Gln Ser
65                  70                  75                  80

Asn Val Phe Lys Asn Leu Thr Ala Thr Leu Ile Val Asn Val Lys Pro
                85                  90                  95

<210> SEQ ID NO 3
<211> LENGTH: 86
<212> TYPE: PRT
<213> ORGANISM: Homo sapiens

<400> SEQUENCE: 3

Pro Arg Leu Ser Ile Gln Lys Asp Ile Leu Thr Ile Lys Ala Asn Thr
1               5                   10                  15

Thr Leu Gln Ile Thr Cys Arg Gly Gln Arg Asp Leu Asp Trp Leu Trp
                20                  25                  30

Pro Asn Asn Gln Ser Gly Ser Glu Gln Arg Val Glu Val Thr Glu Cys
            35                  40                  45

Ser Asp Gly Leu Phe Cys Lys Thr Leu Thr Ile Pro Lys Val Ile Gly
    50                  55                  60

Asn Asp Thr Gly Ala Tyr Lys Cys Phe Tyr Arg Glu Thr Asp Leu Ala
65                  70                  75                  80

Ser Val Ile Tyr Val Tyr
                85

<210> SEQ ID NO 4
<211> LENGTH: 102
<212> TYPE: PRT
<213> ORGANISM: Homo sapiens

<400> SEQUENCE: 4

Val Val Leu Ser Pro Ser His Gly Ile Glu Leu Ser Val Gly Glu Lys
1               5                   10                  15

```
Leu Val Leu Asn Cys Thr Ala Arg Thr Glu Leu Asn Val Gly Ile Asp
            20                  25                  30

Phe Asn Trp Glu Tyr Pro Ser Ser Lys His Gln His Lys Lys Leu Val
            35                  40                  45

Asn Arg Asp Leu Lys Thr Gln Ser Gly Ser Glu Met Lys Lys Phe Leu
 50                  55                  60

Ser Thr Leu Thr Ile Asp Gly Val Thr Arg Ser Asp Gln Gly Leu Tyr
 65                  70                  75                  80

Thr Cys Ala Ala Ser Ser Gly Leu Met Thr Lys Lys Asn Ser Thr Phe
             85                  90                  95

Val Arg Val His Glu Lys
             100

<210> SEQ ID NO 5
<211> LENGTH: 92
<212> TYPE: PRT
<213> ORGANISM: Homo sapiens

<400> SEQUENCE: 5

Phe Val Ala Phe Gly Ser Gly Met Glu Ser Leu Val Glu Ala Thr Val
 1               5                  10                  15

Gly Glu Arg Val Arg Ile Pro Ala Lys Tyr Leu Gly Tyr Pro Pro Pro
            20                  25                  30

Glu Ile Lys Trp Tyr Lys Asn Gly Ile Pro Leu Glu Ser Asn His Thr
            35                  40                  45

Ile Lys Ala Gly His Val Leu Thr Ile Met Glu Val Ser Glu Arg Asp
 50                  55                  60

Thr Gly Asn Tyr Thr Val Ile Leu Thr Asn Pro Ile Lys Ser Glu Lys
 65                  70                  75                  80

Gln Ser His Val Val Ser Leu Val Val Tyr Val Pro
             85                  90

<210> SEQ ID NO 6
<211> LENGTH: 1656
<212> TYPE: DNA
<213> ORGANISM: Artificial
<220> FEATURE:
<223> OTHER INFORMATION: Recombinant DNA encoding chimeric protein FP3
<220> FEATURE:
<221> NAME/KEY: CDS
<222> LOCATION: (1)..(1656)
<220> FEATURE:
<221> NAME/KEY: mat_peptide
<222> LOCATION: (1)..(1656)

<400> SEQUENCE: 6 atg gtc agc tac tgg gac acc ggg gtc ctg ctg tgc gcg ctg ctc agc      48
Met Val Ser Tyr Trp Asp Thr Gly Val Leu Leu Cys Ala Leu Leu Ser
 1               5                  10                  15 tgt ctg ctt ctc aca gga tct agt tcc gga ggt aga cct ttc gta gag      96
Cys Leu Leu Leu Thr Gly Ser Ser Ser Gly Gly Arg Pro Phe Val Glu
            20                  25                  30 atg tac agt gaa atc ccc gaa att ata cac atg act gaa gga agg gag     144
Met Tyr Ser Glu Ile Pro Glu Ile Ile His Met Thr Glu Gly Arg Glu
            35                  40                  45 ctc gtc att ccc tgc cgg gtt acg tca cct aac atc act gtt act tta     192
Leu Val Ile Pro Cys Arg Val Thr Ser Pro Asn Ile Thr Val Thr Leu
 50                  55                  60 aaa aag ttt cca ctt gac act ttg atc cct gat gga aaa cgc ata atc     240
Lys Lys Phe Pro Leu Asp Thr Leu Ile Pro Asp Gly Lys Arg Ile Ile
 65                  70                  75                  80
```

```
tgg gac agt aga aag ggc ttc atc ata tca aat gca acg tac aaa gaa      288
Trp Asp Ser Arg Lys Gly Phe Ile Ile Ser Asn Ala Thr Tyr Lys Glu
                85                  90                  95 ata ggg ctt ctg acc tgt gaa gca aca gtc aat ggg cat ttg tat aag      336
Ile Gly Leu Leu Thr Cys Glu Ala Thr Val Asn Gly His Leu Tyr Lys
        100                 105                 110 aca aac tat ctc aca cat cga caa acc aat aca atc ata gat gtg gtt      384
Thr Asn Tyr Leu Thr His Arg Gln Thr Asn Thr Ile Ile Asp Val Val
            115                 120                 125 ctg agt ccg tct cat gga att gaa cta tct gtt gga gaa aag ctt gtc      432
Leu Ser Pro Ser His Gly Ile Glu Leu Ser Val Gly Glu Lys Leu Val
    130                 135                 140 tta aat tgt aca gca aga act gaa cta aat gtg ggg att gac ttc aac      480
Leu Asn Cys Thr Ala Arg Thr Glu Leu Asn Val Gly Ile Asp Phe Asn
145                 150                 155                 160 tgg gaa tac cct tct tcg aag cat cag cat aag aaa ctt gta aac cga      528
Trp Glu Tyr Pro Ser Ser Lys His Gln His Lys Lys Leu Val Asn Arg
                165                 170                 175 gac cta aaa acc cag tct ggg agt gag atg aag aaa ttt ttg agc acc      576
Asp Leu Lys Thr Gln Ser Gly Ser Glu Met Lys Lys Phe Leu Ser Thr
        180                 185                 190 tta act ata gat ggt gta acc cgg agt gac caa gga ttg tac acc tgt      624
Leu Thr Ile Asp Gly Val Thr Arg Ser Asp Gln Gly Leu Tyr Thr Cys
            195                 200                 205 gca gca tcc agt ggg ctg atg acc aag aag aac agc aca ttt gtc agg      672
Ala Ala Ser Ser Gly Leu Met Thr Lys Lys Asn Ser Thr Phe Val Arg
    210                 215                 220 gtc cat gaa aac ctt tct gtt gct ttt gga agt ggc atg gaa tct ctg      720
Val His Glu Asn Leu Ser Val Ala Phe Gly Ser Gly Met Glu Ser Leu
225                 230                 235                 240 gtg gaa gcc acg gtg ggg gag cgt gtc aga atc cct gcg aag tac ctt      768
Val Glu Ala Thr Val Gly Glu Arg Val Arg Ile Pro Ala Lys Tyr Leu
                245                 250                 255 ggt tac cca ccc cca gaa ata aaa tgg tat aaa aat gga ata ccc ctt      816
Gly Tyr Pro Pro Pro Glu Ile Lys Trp Tyr Lys Asn Gly Ile Pro Leu
        260                 265                 270 gag tcc aat cac aca att aaa gcg ggg cat gta ctg acg att atg gaa      864
Glu Ser Asn His Thr Ile Lys Ala Gly His Val Leu Thr Ile Met Glu
            275                 280                 285 gtg agt gaa aga gac aca gga aat tac act gtc atc ctt acc aat ccc      912
Val Ser Glu Arg Asp Thr Gly Asn Tyr Thr Val Ile Leu Thr Asn Pro
    290                 295                 300 att tca aag gag aag cag agc cat gtg gtc tct ctg gtt gtg tat gtc      960
Ile Ser Lys Glu Lys Gln Ser His Val Val Ser Leu Val Val Tyr Val
305                 310                 315                 320 cca ccg ggc ccg ggc gac aaa act cac aca tgc cca ctg tgc cca gca     1008
Pro Pro Gly Pro Gly Asp Lys Thr His Thr Cys Pro Leu Cys Pro Ala
                325                 330                 335 cct gaa ctc ctg ggg gga ccg tca gtc ttc ctc ttc ccc cca aaa ccc     1056
Pro Glu Leu Leu Gly Gly Pro Ser Val Phe Leu Phe Pro Pro Lys Pro
        340                 345                 350 aag gac acc ctc atg atc tcc cgg acc cct gag gtc aca tgc gtg gtg     1104
Lys Asp Thr Leu Met Ile Ser Arg Thr Pro Glu Val Thr Cys Val Val
            355                 360                 365 gtg gac gtg agc cac gaa gac cct gag gtc aag ttc aac tgg tac gtg     1152
Val Asp Val Ser His Glu Asp Pro Glu Val Lys Phe Asn Trp Tyr Val
    370                 375                 380 gac ggc gtg gag gtg cat aat gcc aag aca aag ccg cgg gag gag cag     1200
Asp Gly Val Glu Val His Asn Ala Lys Thr Lys Pro Arg Glu Glu Gln
```

-continued

```
                385                 390                 395                 400
tac aac agc acg tac cgt gtg gtc agc gtc ctc acc gtc ctg cac cag         1248
Tyr Asn Ser Thr Tyr Arg Val Val Ser Val Leu Thr Val Leu His Gln
                405                 410                 415 gac tgg ctg aat ggc aag gag tac aag tgc aag gtc tcc aac aaa gcc         1296
Asp Trp Leu Asn Gly Lys Glu Tyr Lys Cys Lys Val Ser Asn Lys Ala
            420                 425                 430 ctc cca gcc ccc atc gag aaa acc atc tcc aaa gcc aaa ggg cag ccc         1344
Leu Pro Ala Pro Ile Glu Lys Thr Ile Ser Lys Ala Lys Gly Gln Pro
        435                 440                 445 cga gaa cca cag gtg tac acc ctg ccc cca tcc cgg gat gag ctg acc         1392
Arg Glu Pro Gln Val Tyr Thr Leu Pro Pro Ser Arg Asp Glu Leu Thr
    450                 455                 460 aag aac cag gtc agc ctg acc tgc cta gtc aaa ggc ttc tat ccc agc         1440
Lys Asn Gln Val Ser Leu Thr Cys Leu Val Lys Gly Phe Tyr Pro Ser
465                 470                 475                 480 gac atc gcc gtg gag tgg gag agc aat ggg cag ccg gag aac aac tac         1488
Asp Ile Ala Val Glu Trp Glu Ser Asn Gly Gln Pro Glu Asn Asn Tyr
                485                 490                 495 aag gcc acg cct ccc gtg ctg gac tcc gac ggc tcc ttc ttc ctc tac         1536
Lys Ala Thr Pro Pro Val Leu Asp Ser Asp Gly Ser Phe Phe Leu Tyr
            500                 505                 510 agc aag ctc acc gtg gac aag agc agg tgg cag cag ggg aac gtc ttc         1584
Ser Lys Leu Thr Val Asp Lys Ser Arg Trp Gln Gln Gly Asn Val Phe
        515                 520                 525 tca tgc tcc gtg atg cat gag gct ctg cac aac cac tac acg cag aag         1632
Ser Cys Ser Val Met His Glu Ala Leu His Asn His Tyr Thr Gln Lys
    530                 535                 540 agc ctc tcc ctg tct ccg ggt aaa                                         1656
Ser Leu Ser Leu Ser Pro Gly Lys
545                 550

<210> SEQ ID NO 7
<211> LENGTH: 552
<212> TYPE: PRT
<213> ORGANISM: Artificial
<220> FEATURE:
<223> OTHER INFORMATION: Synthetic Construct (chimeric protein FP3)
<220> FEATURE:
<221> NAME/KEY: CHAIN
<222> LOCATION: (1)..(552)

<400> SEQUENCE: 7

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125
```

```
Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
210                 215                 220

Val His Glu Asn Leu Ser Val Ala Phe Gly Ser Gly Met Glu Ser Leu
225                 230                 235                 240

Val Glu Ala Thr Val Gly Glu Arg Val Arg Ile Pro Ala Lys Tyr Leu
                245                 250                 255

Gly Tyr Pro Pro Pro Glu Ile Lys Trp Tyr Lys Asn Gly Ile Pro Leu
            260                 265                 270

Glu Ser Asn His Thr Ile Lys Ala Gly His Val Leu Thr Ile Met Glu
        275                 280                 285

Val Ser Glu Arg Asp Thr Gly Asn Tyr Thr Val Ile Leu Thr Asn Pro
290                 295                 300

Ile Ser Lys Glu Lys Gln Ser His Val Val Ser Leu Val Val Tyr Val
305                 310                 315                 320

Pro Pro Gly Pro Gly Asp Lys Thr His Thr Cys Pro Leu Cys Pro Ala
                325                 330                 335

Pro Glu Leu Leu Gly Gly Pro Ser Val Phe Leu Phe Pro Pro Lys Pro
            340                 345                 350

Lys Asp Thr Leu Met Ile Ser Arg Thr Pro Glu Val Thr Cys Val Val
        355                 360                 365

Val Asp Val Ser His Glu Asp Pro Glu Val Lys Phe Asn Trp Tyr Val
370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
            420                 425                 430

Leu Pro Ala Pro Ile Glu Lys Thr Ile Ser Lys Ala Lys Gly Gln Pro
        435                 440                 445

Arg Glu Pro Gln Val Tyr Thr Leu Pro Pro Ser Arg Asp Glu Leu Thr
450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Ala Thr Pro Pro Val Leu Asp Ser Asp Gly Ser Phe Phe Leu Tyr
            500                 505                 510

Ser Lys Leu Thr Val Asp Lys Ser Arg Trp Gln Gln Gly Asn Val Phe
        515                 520                 525

Ser Cys Ser Val Met His Glu Ala Leu His Asn His Tyr Thr Gln Lys
530                 535                 540

Ser Leu Ser Leu Ser Pro Gly Lys
```

-continued

```
545                    550

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
cctttcgtag agatgtacag tga                                          23

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
tatgattgta ttggtttgtc cat                                          23

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
gatgtggttc tgagtccgtc tca                                          23

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
cggtgggaca tacacaacca ga                                           22

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
gacaaaactc acacatgccc act                                          23

<210> SEQ ID NO 13
<211> LENGTH: 24
<212> TYPE: DNA
<213> ORGANISM: Artificial
<220> FEATURE:
<223> OTHER INFORMATION: Primer

<400> SEQUENCE: 13
tcatttaccc ggagacaggg agag                                         24
```